United States Patent
Santarelli et al.

(10) Patent No.: US 12,102,427 B2
(45) Date of Patent: Oct. 1, 2024

(54) USER AUTHENTICATION VIA IN-EAR ACOUSTIC MEASUREMENTS

(71) Applicant: BOSE CORPORATION, Framingham, MA (US)

(72) Inventors: Keith Robert Santarelli, Wakefield, MA (US); Andrew Todd Sabin, Chicago, IL (US); Brian J. Maguire, Franklin, MA (US); John Allen Rule, Berlin, MA (US); Robert Heinz Haslinger, Arlington, MA (US); Andrew D. Dominijanni, Newton, MA (US)

(73) Assignee: BOSE CORPORATION, Framingham, MA (US)

( * ) Notice: Subject to any disclaimer, the term of this patent is extended or adjusted under 35 U.S.C. 154(b) by 543 days.

(21) Appl. No.: 17/353,981

(22) Filed: Jun. 22, 2021

(65) Prior Publication Data

US 2021/0393168 A1    Dec. 23, 2021

Related U.S. Application Data

(60) Provisional application No. 63/042,286, filed on Jun. 22, 2020.

(51) Int. Cl.
| | |
|---|---|
| *A61B 5/1171* | (2016.01) |
| *A61B 5/00* | (2006.01) |
| *G06F 21/32* | (2013.01) |
| *H04R 1/10* | (2006.01) |
| *H04R 25/00* | (2006.01) |
| *G10L 17/24* | (2013.01) |

(52) U.S. Cl.
CPC ......... *A61B 5/1171* (2016.02); *A61B 5/6815* (2013.01); *G06F 21/32* (2013.01); *H04R 1/1016* (2013.01); *H04R 25/30* (2013.01); *G10L 17/24* (2013.01)

(58) Field of Classification Search
None
See application file for complete search history.

(56) References Cited

U.S. PATENT DOCUMENTS

| | | | | |
|---|---|---|---|---|
| 2004/0215968 A1* | 10/2004 | Rodwell | ................ | H04M 1/67 713/186 |
| 2018/0376234 A1* | 12/2018 | Petrank | ................ | H04R 1/1083 |
| 2020/0411014 A1* | 12/2020 | Asher | ................ | G10L 17/04 |

OTHER PUBLICATIONS

Gao et al., "EarEcho: Using Ear Canal Echo for Wearable Authentication", Proc. ACM Interact. Mob. Wearable Ubiquitous Technol., vol. 3, No. 3, Article 81, Sep. 2019.

* cited by examiner

*Primary Examiner* — Antim G Shah
(74) *Attorney, Agent, or Firm* — Lando and Anastasi, LLP

(57) ABSTRACT

Techniques for user authentication via in-ear acoustic measurements are disclosed. An in-ear device emits an acoustic signal and detects an otic response to the acoustic signal. A user signature is generated based at least on the otic response to the acoustic signal. The user signature is compared with a reference signature, to determine whether the in-ear device has changed users.

21 Claims, 11 Drawing Sheets

USER AUTHENTICATION VIA IN-EAR ACOUSTIC MEASUREMENTS

RELATED APPLICATIONS

This application claims the benefit of U.S. Provisional Patent Application Ser. No. 63/042,286, titled "USER AUTHENTICATION VIA IN-EAR ACOUSTIC MEASUREMENTS," filed Jun. 22, 2020, which is hereby incorporated by reference in its entirety.

BACKGROUND

An in-ear device is a device that is either partly or wholly inserted into a user's ear and used to emit sounds into the ear. For example, an in-ear device may be an earbud-type device that inserts into a user's ear and emits sounds such as music, voice, etc. An in-ear device may be wired, i.e., have a cable that operatively connects the in-ear device to another device such as a portable audio device or transmitter, a phone, a computer, etc. Alternatively, an in-ear device may be wireless, i.e., capable of communicating with another device without a cable connection. For example, an in-ear device may include Bluetooth™, Wi-Fi, and/or another kind of wireless communication hardware using radio frequency (RF), induction, and/or another kind of wireless transmission transmission/reception medium. Some in-ear devices are general-purpose devices for listening to music, making phone calls, etc. Other in-ear devices are special-purpose devices, such as telephony devices and medical hearing aids. A general-purpose device may also include special-purpose features (e.g., a general-purpose earbud that is also capable of amplifying external noise), and a special-purpose device may also be capable of performing some general purpose functions (e.g., a hearing aid that is also capable of music playback).

As used herein, the term "hearing aid" refers to a medical device that approved by a medical body to treat hearing loss, the cost of which may be wholly or partly subsidized by medical insurance. Untreated hearing loss is associated with comorbidities such as falls, depression, cognitive impairment, and dementia. Thus, insurance companies may wish to provide coverage for hearing aids, in order to reduce total claim costs. However, in some cases, an insured individual may purchase an insurance-subsidized hearing aid for another person who is not covered by the health insurance or who otherwise does not qualify for an insurance-subsidized hearing aid. For example, an individual who can demonstrate sufficient hearing loss to obtain an insurance-subsidized hearing aid may give the hearing aid to their uninsured parent or other relative or friend, or sell the device to a third party for profit. Insurance fraud is therefore a concern when providing insurance subsidies for hearing aids.

Approaches described in this section have not necessarily been conceived and/or pursued prior to the filing of this application. Accordingly, unless otherwise indicated, approaches described in this section should not be construed as prior art.

TECHNICAL FIELD

The present disclosure relates generally to in-ear devices, and more particularly to authenticating users of in-ear devices.

SUMMARY

One or more embodiments include components and techniques for authenticating users of in-ear devices, using an in-ear device that is able to both emit signals and detect otic responses to those signals. User signatures are based on the otic responses and may be used to authenticate a user, i.e., to confirm that the in-ear device has not impermissibly changed users. Authentication techniques described herein may thus be used to confirm, for example, that a hearing aid is being used by the intended individual. Alternatively or additionally, for an in-ear device that is used by multiple users (e.g., a set of commercial earbuds) a user signature may be used to determine one or more user-specific presets (e.g., channel presets, virtual assistant settings, volume and/or equalization settings, etc.) to apply for that user. Alternatively or additionally, a user signature may be used as a biometric passcode in lieu of (or in addition to) an alphanumeric password (e.g., to unlock a device, login to a website, etc.).

In general, in one aspect, one or more non-transitory computer-readable media store instructions that, when executed by one or more processors, cause: emitting, by an in-ear device, a first acoustic signal; detecting, by the in-ear device, a first otic response to the first acoustic signal; generating a first user signature, based at least on the first otic response to the first acoustic signal; and performing a comparison of the first user signature and a second user signature associated with the in-ear device, to determine whether the in-ear device has changed users. The first acoustic signal may be one of multiple acoustic signals emitted by the in-ear device during a signature generation session; the first otic response may be one of multiple otic responses, associated respectively with the multiple acoustic signals, detected during the signature generation session; and generating the first user signature may include computing the first user signature as a function of at least the multiple otic responses. The in-ear device may be configured to generate the multiple acoustic signals and detect the multiple otic responses over multiple instances of inserting the in-ear device into an ear during the signature generation session.

The one or more non-transitory computer-readable media may further store instructions that, when executed by one or more processors, cause: emitting, by the in-ear device, a second acoustic signal; detecting, by the in-ear device, a second otic response the second acoustic signal; and generating the second user signature as a reference signature for user authentication, based at least on the second otic response to the second acoustic signal.

The one or more non-transitory computer-readable media may further store instructions that, when executed by one or more processors, cause: determining, based on the comparison of the first user signature and the second user signature, that the in-ear device has changed users; and responsive to determining that the in-ear device has changed users, transmitting an alert to an entity that provides one or more services associated with the in-ear device. The in-ear device may be a medical hearing aid and the entity that provides one or more services associated with the in-ear device may be a medical insurance provider.

The one or more non-transitory computer-readable media may further store instructions that, when executed by one or more processors, cause: detecting a drift in otic responses of an ear of a user, over multiple signature generation sessions; and responsive to detecting the drift in otic responses of the ear, updating a reference user signature for the user to reflect the drift.

In general, in one aspect, a system includes at least one device including one or more processors. The system is configured to perform operations including: emitting, by an in-ear device, a first acoustic signal; detecting, by the in-ear device, a first otic response to the first acoustic signal; generating a first user signature, based at least on the first otic response to the first acoustic signal; and performing a comparison of the first user signature and a second user signature associated with the in-ear device, to determine whether the in-ear device has changed users. The first acoustic signal may be one of multiple acoustic signals emitted by the in-ear device during a signature generation session; the first otic response may be one of multiple otic responses, associated respectively with the multiple acoustic signals, detected during the signature generation session; and generating the first user signature may include computing the first user signature as a function of at least the multiple otic responses. The in-ear device may be configured to generate the multiple acoustic signals and detect the multiple otic responses over multiple instances of inserting the in-ear device into an ear during the signature generation session.

The operations may further include: emitting, by the in-ear device, a second acoustic signal; detecting, by the in-ear device, a second otic response the second acoustic signal; and generating the second user signature as a reference signature for user authentication, based at least on the second otic response to the second acoustic signal.

The operations may further include: determining, based on the comparison of the first user signature and the second user signature, that the in-ear device has changed users; and responsive to determining that the in-ear device has changed users, transmitting an alert to an entity that provides one or more services associated with the in-ear device. The in-ear device may be a medical hearing aid and the entity that provides one or more services associated with the in-ear device may be a medical insurance provider.

The operations may further include: detecting a drift in otic responses of an ear of a user, over a plurality of signature generation sessions; and responsive to detecting the drift in otic responses of the ear, updating a reference user signature for the user to reflect the drift.

In general, in one aspect, a method includes: emitting, by an in-ear device, a first acoustic signal; detecting, by the in-ear device, a first otic response to the first acoustic signal; generating a first user signature, based at least on the first otic response to the first acoustic signal; and performing a comparison of the first user signature and a second user signature associated with the in-ear device, to determine whether the in-ear device has changed users. The first acoustic signal may be one of multiple acoustic signals emitted by the in-ear device during a signature generation session; the first otic response may be one of multiple otic responses, associated respectively with the multiple acoustic signals, detected during the signature generation session; and generating the first user signature may include computing the first user signature as a function of at least the multiple otic responses. The in-ear device may be configured to generate the multiple acoustic signals and detect the multiple otic responses over multiple instances of inserting the in-ear device into an ear during the signature generation session.

The method may further include: emitting, by the in-ear device, a second acoustic signal; detecting, by the in-ear device, a second otic response the second acoustic signal; and generating the second user signature as a reference signature for user authentication, based at least on the second otic response to the second acoustic signal.

The method may further include: determining, based on the comparison of the first user signature and the second user signature, that the in-ear device has changed users; and responsive to determining that the in-ear device has changed users, transmitting an alert to an entity that provides one or more services associated with the in-ear device. The in-ear device may be a medical hearing aid and the entity that provides one or more services associated with the in-ear device may be a medical insurance provider.

The method may further include: detecting a drift in otic responses of an ear of a user, over multiple signature generation sessions; and responsive to detecting the drift in otic responses of the ear, updating a reference user signature for the user to reflect the drift.

In some aspects, a user signature may be based, in part, on one or more kinds of biometric data other than otic responses.

One or more embodiments described in this Specification and/or recited in the claims may not be included in this General Overview section.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures.

DETAILED DESCRIPTION

System Architecture

Figure 1:
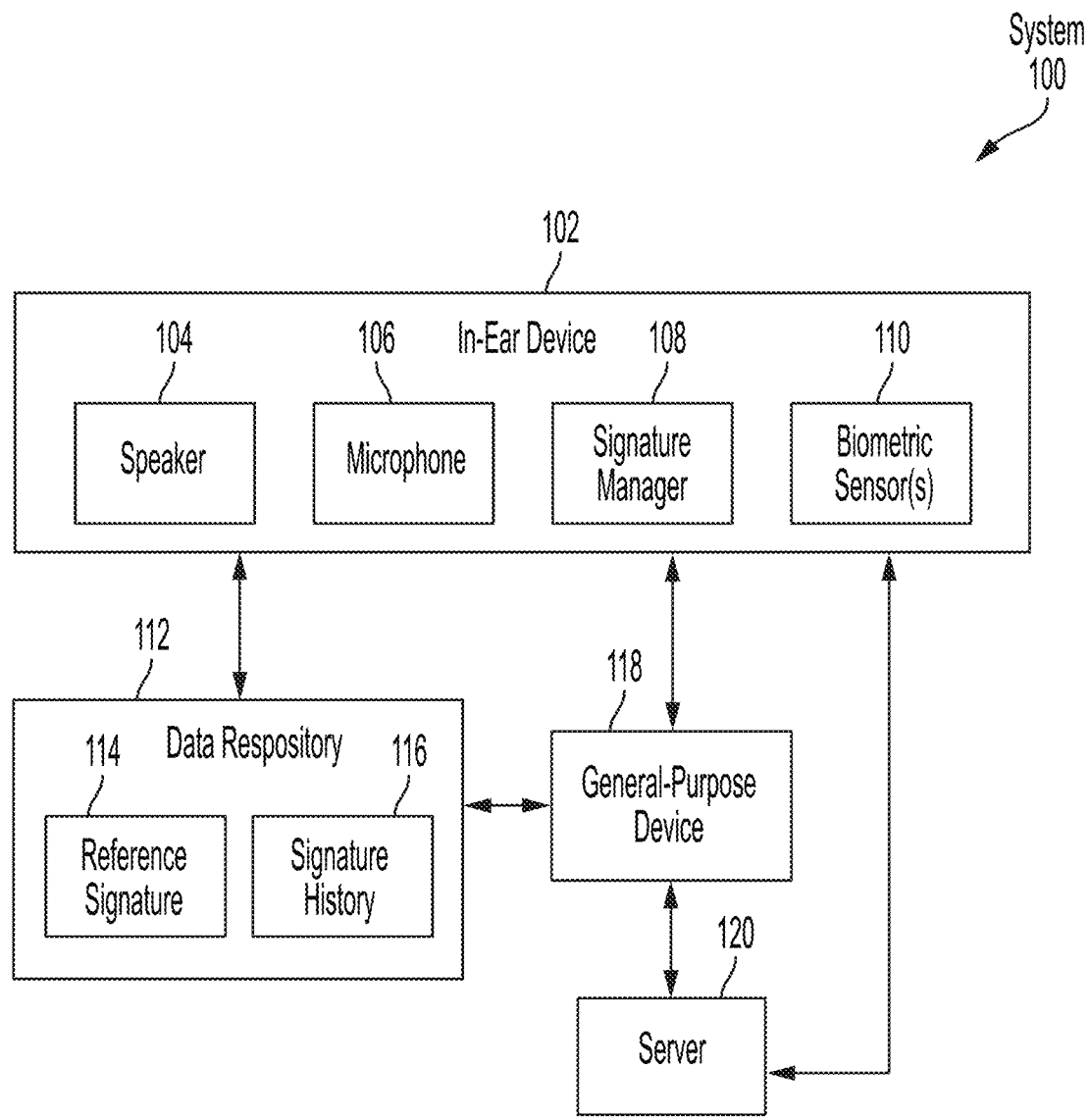
FIG. 1 is a block diagram of an example of a system according to an embodiment.

FIG. 1 is a block diagram of an example of a system 100 according to an embodiment. In an embodiment, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

As illustrated in FIG. 1, an in-ear device 102 includes a speaker 104 and a microphone 106. The in-ear device 102 may be a special-purpose device, such as a hearing aid or telephony device. Alternatively, the in-ear device 102 may be a general-purpose device, such as a commercial earbud configured to receive voice and/or music audio from a smartphone, tablet, computer, smart speaker, or other kind of device. If the in-ear device 102 is a general-purpose device, it may also include special-purpose functions, such as the ability to amplify environmental audio. If the in-ear device 102 is a special-purpose device, it may also be capable of general-purpose functions, such as receiving voice and/or music audio. While embodiments described herein refer to an in-ear device 102, other examples may employ an over-the-ear device, such as a closed-back or open-back over-the-ear headset, which may not include any component that physically inserts into the user's ear.

The speaker 104 is integrated into the in-ear device 102 and configured to emit signals into a user's ear, e.g., into the ear canal. Many different kinds of signals may be used to generate otic responses as described herein. For example, the signal may include white noise, pink noise, and/or some other acoustic pattern emitted over a period of time (e.g., 10 seconds or another duration). Alternatively or additionally, the signal may include a tone, chirp, or other kind of sound. The signal may serve a dual purpose of informing the user that the in-ear device 102 is situated in the ear and/or that the authentication process is starting. The microphone 106 also is integrated into the in-ear device 102 and configured to detect otic responses to the signals emitted by the speaker 104. For example, if a signal is emitted into the user's ear canal, the microphone 106 receives audio corresponding to the otic response within the ear canal.

The in-ear device 102 (or alternatively, another device operatively connected to the in-ear device 102, such as the general-purpose device 118 and/or server 120 described below) includes a signature manager 108. The signature manager 108 is configured to generate user signatures, based at least in part on the otic responses detected by the microphone 106. A user signature refers to data (i.e., one or more data structures storing one or more values) that uniquely identifies a user, to at least a reasonable degree of certainty. In some examples, a user signature is based on data from two ears, i.e., a combination of otic responses detected in the right ear and the left ear, using different in-ear devices (which may include two physically separate devices or a single physical device having portions extending to each ear). For example, a user signature may be a function, at least in part, of otic responses detected in a user's right and left ears, in response to acoustic signals emitted by a matched pair of in-ear devices. Alternatively or additionally, a user signature may be based on multiple otic responses, detected in response to multiple acoustic signatures emitted over the course of a signature generation session. Some examples of operations for generating user signatures are discussed in further detail below.

In some cases, a user signature may also be based, at least in part, on additional biometric data gathered by one or more additional biometric sensor(s) 110. For example, the biometric sensor(s) 110 may include one or more of: a camera configured to obtain video and/or an image for facial recognition and/or ocular image analysis; a fingerprint reader; a thermometer; an odor sensor; and/or another kind of biometric sensor or combination thereof. Combining multiple kinds of biometric data (either in a single function or in separate functions, the results of which may be compared with each other to determine whether they concur with each other) may increase accuracy of user authentication, reducing the incidence of false positives and/or negatives.

In an embodiment, the signature manager 108 is configured to generate a reference signature 114. For example, the reference signature 114 may be a user signature generated during an initialization process of the in-ear device 102. The signature manager 108 may be configured to compare subsequently computed user signatures (referred to herein as "comparison signatures") with the reference signature 114, to identify the user based on the reference signature 114 (e.g., if the system 100 stores multiple reference signatures for multiple users) and/or determine whether the in-ear device 102 has changed users. If the in-ear device 102 has changed users, the signature manager 108 may be configured to generate and transmit an alert (e.g., to a server 120 as described below). Alternatively or additionally, the signature manager 108 may be configured to maintain a signature history 116. The signature history 116 stores data obtained during signature generation sessions over time. The signature history 116 may include user signatures computed at different times and/or may include some or all of the underlying data used to compute user signatures. The signature history 116 may be used to detect drift in user signatures (e.g., drift in otic responses due to subtle changes in otic geometry), as described in further detail below.

Some of the operations described herein may be performed off-device, i.e., by a device other than the in-ear device 102. For example, the system 100 may include a general-purpose device 118, such as a smartphone, tablet, laptop computer, desktop computer, and/or another kind of device. The in-ear device 102 may be configured to transmit data (e.g., otic response data, which the in-ear device 102 may transmit as-is or after some post-processing by the in-ear device 102) to the general-purpose device 118, which may be configured to perform additional operations to generate user signatures. The signature manager 108 may be part of the general-purpose device 118 rather than the in-ear device 102. Some or all of the data described herein may be stored by the general-purpose device 118. If additional biometric data is used to generate user signatures, the general-purpose device 118 may include one or more of the biometric sensor(s) 110.

Alternatively or additionally, the in-ear device 102 and/or general-purpose device 118 may be operatively connected to a server 120 that is configured to perform one or more operations described herein. For example, the server 120 may provide cloud-hosted services for computing and/or authenticating user signatures. The signature manager 108 may be provided as a cloud-hosted service. In some cases, the server 120 may be managed and/or accessible by a medical insurance company, and may be configured to receive alerts if the in-ear device 102 changes users. In general, in an embodiment, operations described herein should not be considered limited to being performed by any specific component of the system 100, with the exception of the in-ear device 102 emitting acoustic signals and detecting corresponding otic responses.

Some or all of the data described herein may be stored in one or more data repositories 112. A data repository 112 is any type of storage unit and/or device (e.g., a file system, database, collection of tables, or any other storage mechanism) for storing data. A data repository 112 may include multiple different storage units and/or devices. The multiple different storage units and/or devices may or may not be of the same type or located at the same physical site. Further, a data repository 112 may be implemented or may execute on the same computing system as one or more other components of the system 100. Alternatively or additionally, a data repository 112 may be implemented or executed on a computing system separate from one or more other components of the system 100. A data repository 112 may be logically integrated with one or more other components of the system 100. Alternatively or additionally, a data repository 112 may be communicatively coupled to one or more other components of the system 100 via a direct connection or via a network. In FIG. 1, a data repository 112 is illustrated as storing various kinds of information. Some or all of this information may be implemented and/or distributed across any of the components of the system 100. However, this information is illustrated within the data repository 112 for purposes of clarity and explanation.

In an embodiment, one or more components of the system 100 are implemented on one or more digital devices. The term "digital device" generally refers to any hardware device that includes one or more processors. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

One or more components of the system 100 may include a user interface. In general, a user interface refers to hardware and/or software configured to facilitate communications between a user and a component (e.g., the in-ear device 102, general-purpose device 118, and/or server 120). A user interface renders user interface elements and receives input via user interface elements. A user interface may be a graphical user interface (GUI), a command line interface (CLI), a haptic interface, a voice command interface, and/or any other kind of interface or combination thereof. Examples of user interface elements include checkboxes, radio buttons, dropdown lists, list boxes, buttons, toggles, text fields, date and time selectors, command lines, sliders, pages, and forms. Different components of a user interface may be specified in different languages. The behavior of user interface elements may be specified in a dynamic programming language, such as JavaScript. The content of user interface elements may be specified in a markup language, such as hypertext markup language (HTML), Extensible Markup Language (XML), or XML User Interface Language (XUL). The layout of user interface elements may be specified in a style sheet language, such as Cascading Style Sheets (CSS). Alternatively or additionally, aspects of a user interface may be specified in one or more other languages, such as Java, Python, Perl, C, C++, and/or any other language or combination thereof.

Figure 2:
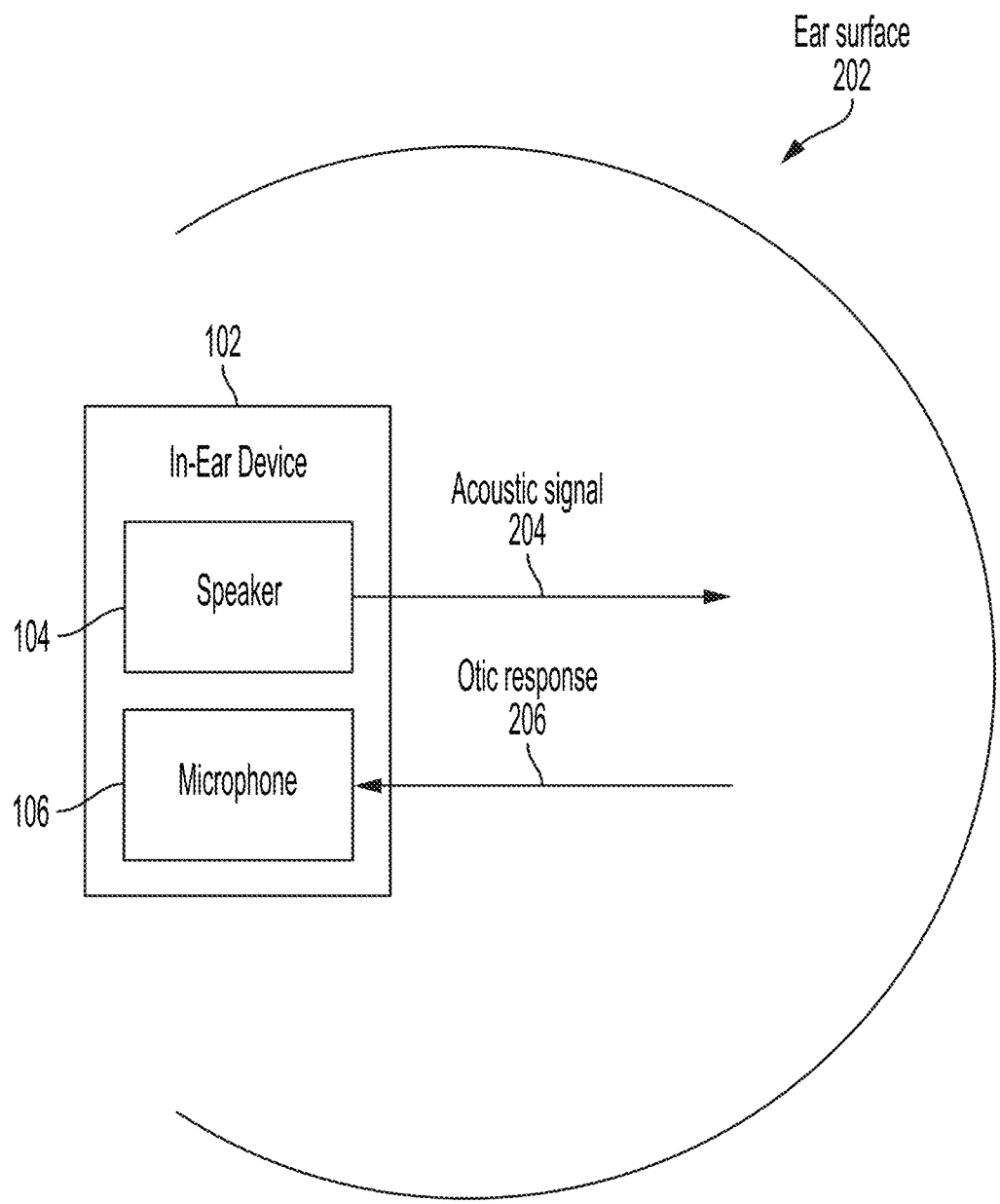
FIG. 2 is a block diagram of an example of detecting an otic response according to an embodiment.

FIG. 2 is a block diagram of an example of detecting an otic response according to an embodiment. As illustrated in FIG. 2, an in-ear device 102 is inserted wholly or partially into a user's ear (e.g., in the manner of an earbud). A speaker 104 emits an acoustic signal 204 that generates an otic response 206 based on the geometry of the ear surface 202 (e.g., the surface of the ear canal and/or other ear anatomy). A microphone 106 of the in-ear device detects the otic response 206. The in-ear device 104 and/or another device operatively connected to the in-ear device 102 compute(s) a user signature based on the otic response 206. The user signature may be based on multiple instances of this process. In other examples, an over-the-ear device (not shown) may be placed over the user's ear. A speaker of the over-the-ear device may emit an acoustic signal into the user's ear, and a microphone of the over-the-ear device may detect the otic response.

Detailed examples are described below for purposes of clarity. Components and/or operations described below should be understood as examples that may not be applicable to one or more embodiments. Accordingly, components and/or operations described below should not be construed as limiting the scope of one or more embodiments.

Transfer Functions

Figure 3A:
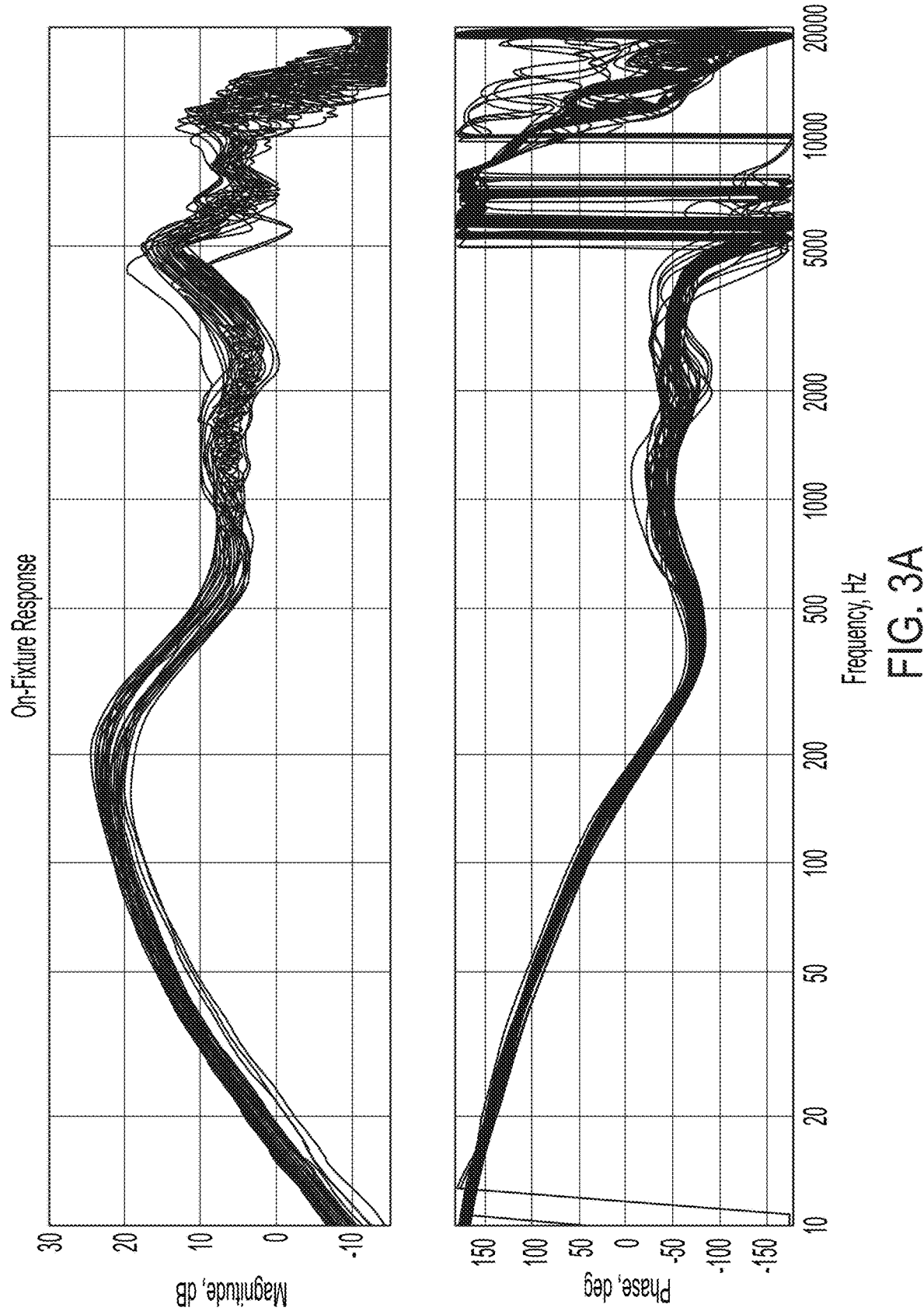
FIG. 3A illustrates examples of graphs of transfer functions according to an embodiment.

FIG. 3A illustrates examples of graphs of transfer functions according to an embodiment. In these examples, the term "on-fixture" refers to the fact that the otic response is detected by the in-ear device, which may also be referred to as a "fixture." Some in-ear devices (e.g., some hearing aids) are "fixtures" in the sense that a fixture is implanted into the skull bone; an additional component may be physically coupled with the fixture.

Figure 3B:
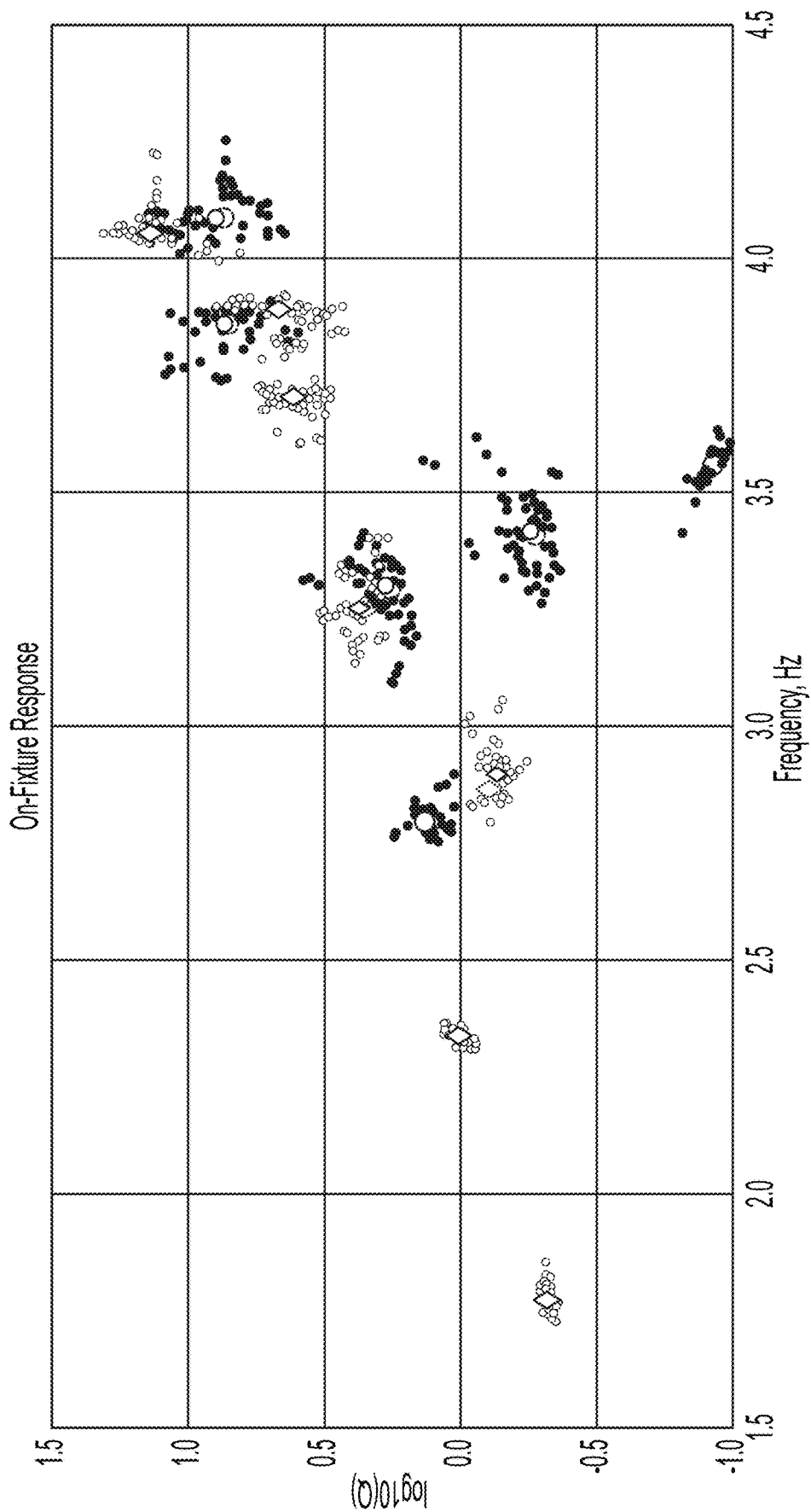
FIG. 3B illustrates an example of a set of coefficients derived from transfer functions according to an embodiment.

Specifically, FIG. 3A illustrates examples of graphs of transfer functions corresponding to magnitude and phase of otic responses, respectively, at different frequencies. The data underlying these examples included eight separate acoustic measurements (i.e., instances of detecting otic responses) for each of sixty users. FIG. 3B illustrates an example of a set of coefficients derived from transfer functions according to an embodiment. In FIG. 3B, otic response data charted on a logarithmic scale indicates that transfer function measurements and optimal parameter sets for the eight measurements tend to cluster around nominal values. These charts thus demonstrate the practicality of using such a transfer function as a signature for identifying a user.

Figure 4:
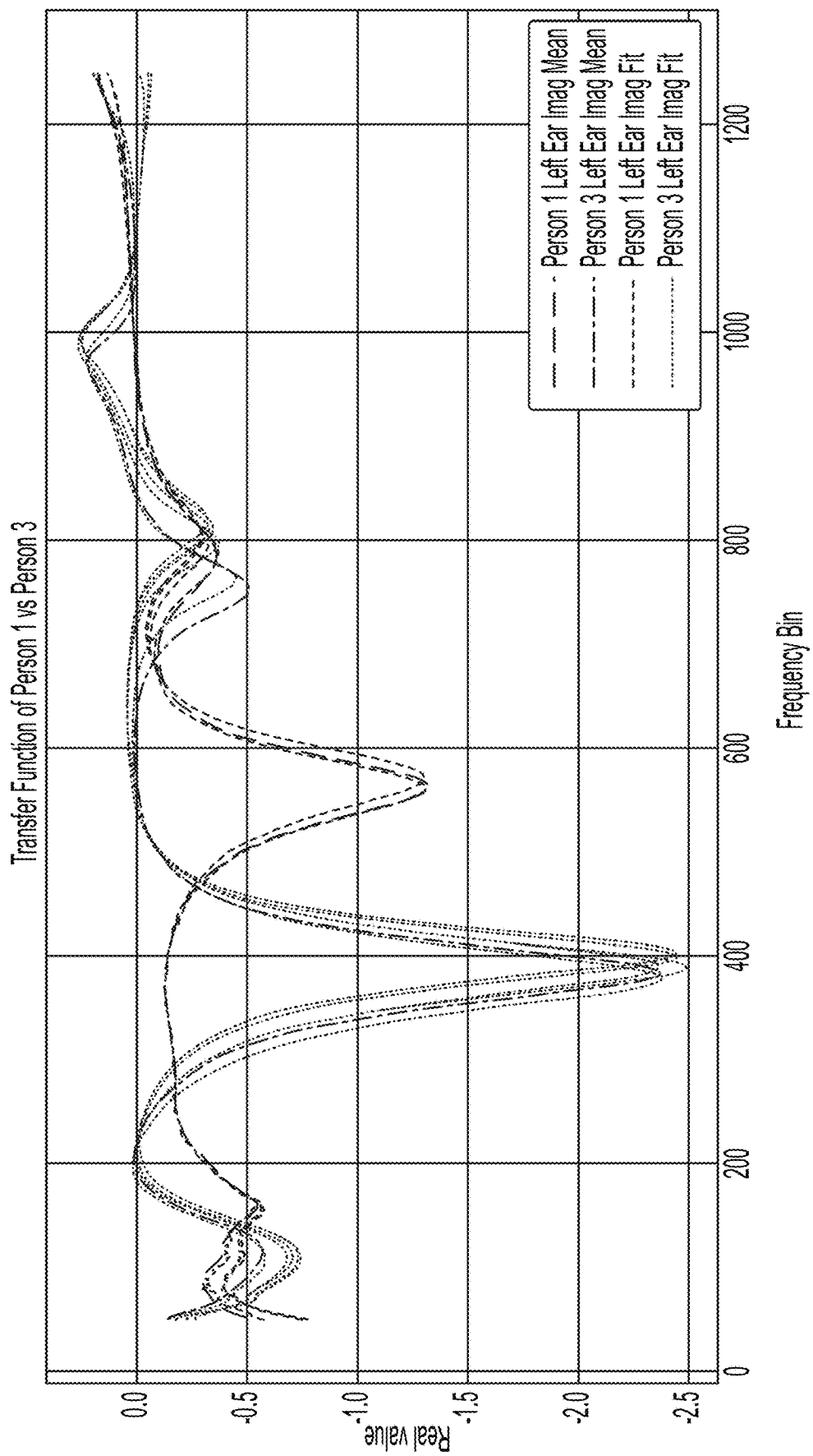
FIG. 4 illustrates an example of a graph of transfer functions according to an embodiment.

FIG. 4 illustrates an example of a graph of transfer functions according to an embodiment. Specifically, FIG. 4 illustrates an example of a graph of transfer functions based on otic responses of the left ears of two separate individuals, over multiple "fits" (i.e., iterations of detecting otic responses). The legend in FIG. 4 indicates which lines represent the means of the first four fits of the individuals; in some embodiments, these lines may correspond to reference signatures. The remaining lines are the remaining fits, which may correspond to comparison signatures. FIG. 4 illustrates how the otic responses cluster over multiple fits, providing a high degree of consistency in the user signature. Based on the data underlying these transfer functions, when combining signatures for both ears, there may be a one in three hundred ($\frac{1}{300}$ or 0.33%) or less chance of misidentifying two people as the same person. If one measurement is taken per day over the course of a week, the odds of a false match drop to one in one hundred thousand ($\frac{1}{100,000}$ or 0.001%). In many use cases, these odds provide a sufficiently rigorous basis for user authentication. In addition, techniques described herein (for example, using additional biometric data to enhance or confirm a user signature) may further decrease the odds of a false match. The odds of a mismatch may be significantly decreased when combining signatures for both ears.

Authentication Metric

User authentication is based on a comparison of a comparison signature with a reference signature. The reference signature is a previously computed user signature that is used as a reference for authenticating subsequently computed comparison signatures. A reference signature may have the same data type or a different data type as a comparison signature. For example, the data type of a reference signature may include more or less data and/or metadata than the data type of a comparison signature. A reference signature may include information about a standard deviation based on the data used to generate the reference signature. Alternatively or additionally, a reference signature may be based on a different number of fits than a comparison signature. For example, a reference signature may be computed as a function of multiple fits (e.g., six fits or a different number of multiple fits) while a comparison signature may be computed as a function of just one fit or another number of fits that may be less than the number of fits used to generate the reference signature.

As described above, user signatures may be based on one or more transfer functions. Alternatively, another kind of computation may be used. Comparing a comparison signature with a reference signature may employ a classification algorithm (e.g., a static function and/or a machine learning model as described in further detail below). The classification algorithm computes a metric that is an indicator of whether the comparison signature originates from the same ear as the reference signature or a different ear. For example, the metric may be based on a weighted residual between the comparison signature and the reference signature. The classification algorithm may be a binary classifier that reports one of yes/no, true/false, 1/0, etc. Alternatively or additionally, the classification algorithm may produce a confidence metric that is compared with one or more confidence thresholds. Many different kinds of classifiers may be used and embodiments should not be considered limited to a specific kind of classifier.

In an embodiment, the classification metric is a modified form of a log likelihood from a normal distribution. The mean and standard deviation curves may be computed from a number of fits. In one series of tests, the mean and standard deviation curves were computed from six fits. A modified log likelihood may then be computed for each frequency in the curve. Those likelihoods may then be summed to produce a similarity metric. For example, the following formula may be used:

$$D = \sum_i \frac{(x_i - \mu_i)^2}{2\sigma_i^2}$$

where $\mu_i$ is the i-th frequency bin for mean curve obtained from the fits, $\sigma_i$ is the standard deviation of the i-th frequency bin over the fits, and $x_i$ is the i-th frequency bin for the measurement transfer function being compared to the reference signature. Embodiments should not be considered limited to this particular equation or general formulation.

Figure 5:
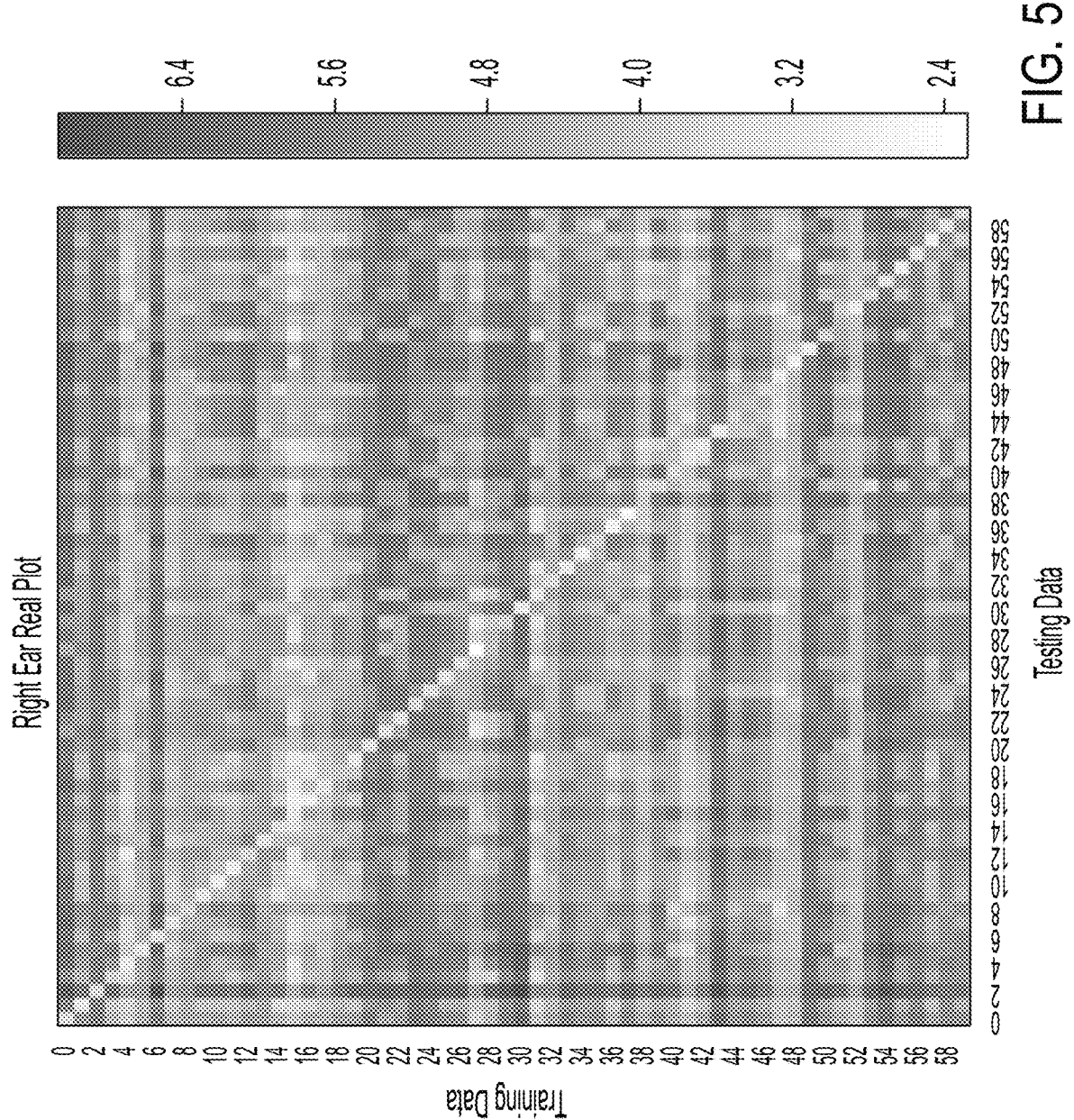
FIG. 5 illustrates an example of an average residual charts according to an embodiment.

FIG. 5 illustrates an example of an average residual chart according to an embodiment, computed using the formula described above. In this example, for each user in a set of 60 users, a total of eight fits each was performed. For each user, a reference signature was generated using six independent fits per ear. Subsequently, the remaining two independent fits per ear were used as comparison signatures, to compute distance metrics for every combination of one user's reference signature compared to each of the users' respective comparison signatures. Specifically, FIG. 5 graphically illustrates the average residual from two matrixes: a first matrix that was generated by computing distance metrics between each user's reference signature and each user's first comparison signature (i.e., from the seventh fit, in this example); and a second matrix that was generated by computing distance metrics between each user's reference signature and each user's second comparison signature (i.e., from the eighth fit, in this example). The matrix illustrated in FIG. 5 is the average of the two matrixes. Thus, each small square represents the average residual that is computed by comparing the signature of user i (the rows of the Figure) with the two comparison signatures of user j (the columns of the Figure). The bright diagonal stripe in FIG. 5 indicates that the residual is substantially less when the comparison signature and reference signature come from the same user than from different users. Accordingly, a classifier used for user authentication may be based on a classification threshold, where the comparison signature and reference signature are predicted to come from the same ear if the distance metric is below the threshold.

Figure 6A:
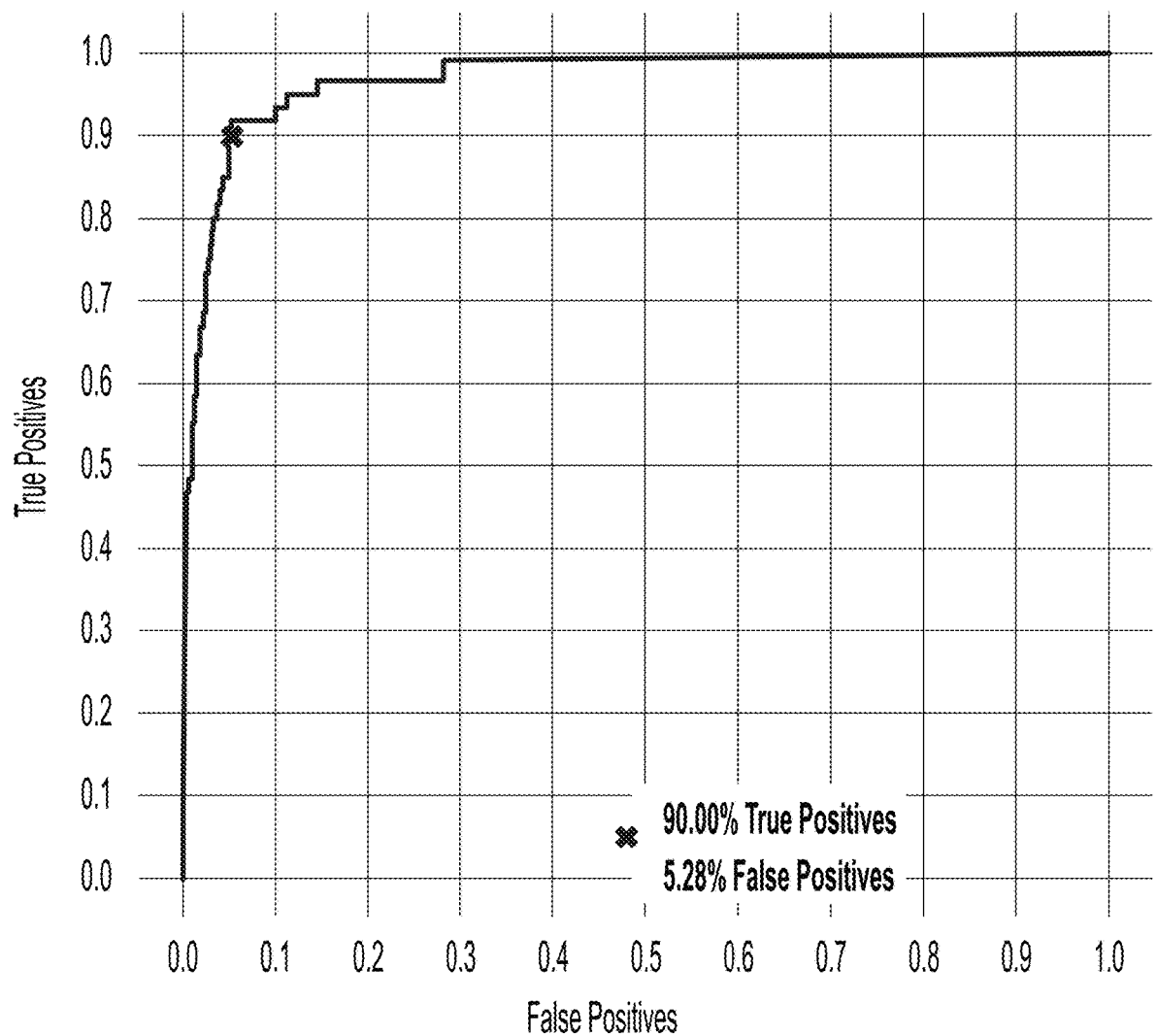
FIGS. 6A-6B illustrate examples of graphs of receiver operating curves (ROC's) according to an embodiment.
Figure 6B:
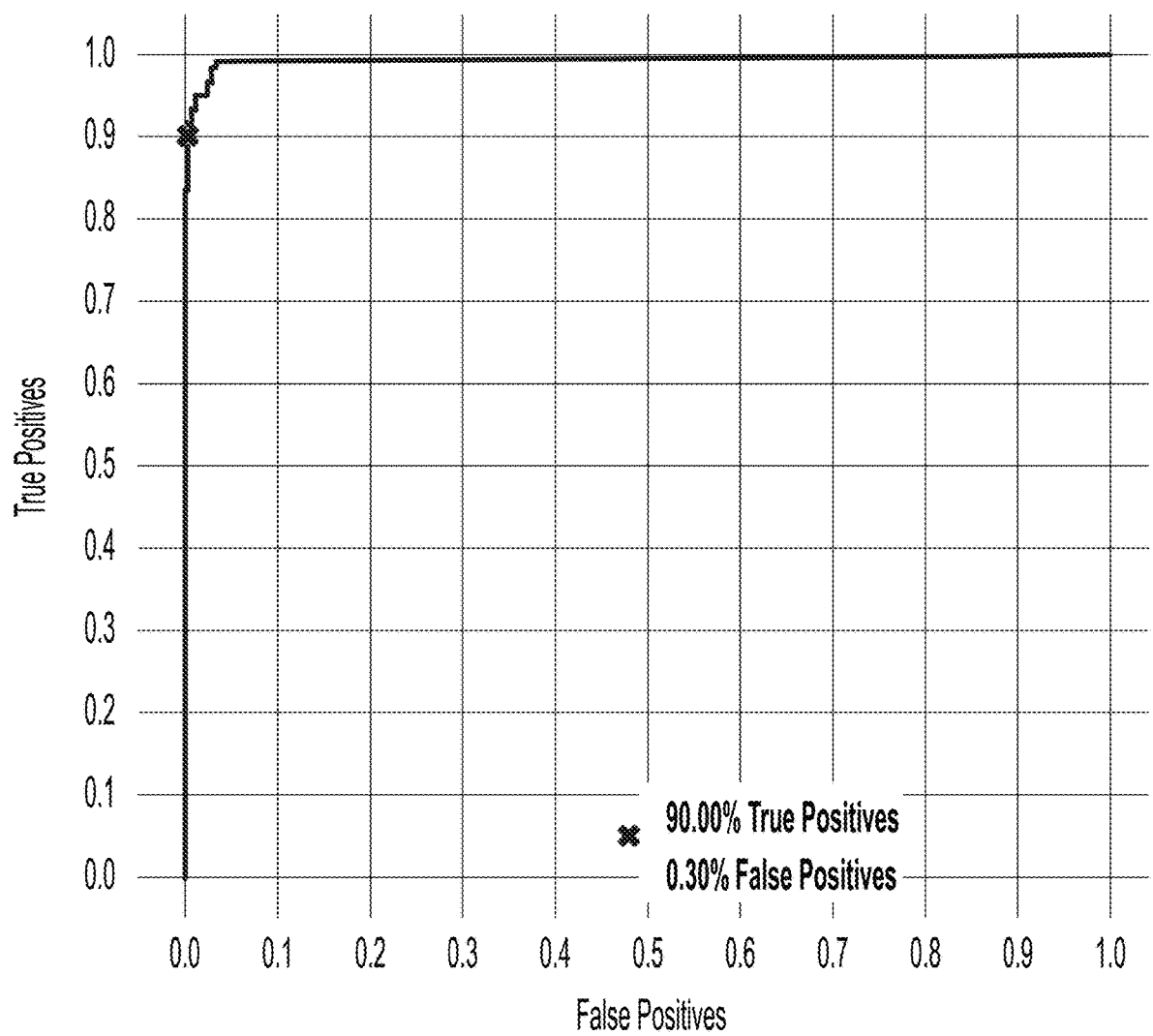

FIGS. 6A-6B illustrate examples of graphs of receiver operating curves (ROC's) according to an embodiment. Specifically, FIG. 6A illustrates an example of an ROC when classifying a comparison signature against a reference signature for a single ear (in this example, the right ear). FIG. 6B illustrates an example of an ROC when classifying comparison signatures against reference signatures for both ears. In these examples, a true positive indicates an accurate classification of the comparison signature as coming from the same ear as the reference signature. A false positive indicates an inaccurate classification of the comparison signature as coming from the same ear as the reference signature when the device has been placed in a different user's ear. In the example of FIG. 6B, if classification for either ear indicated that the in-ear device has changed ears, then the overall classification was negative (even if the classification for one of the ears was positive, which was assumed to be a false positive). These examples illustrate that the false positive rate is significantly lower when classification is based on two ears rather than just one ear. The false positive rate may be even lower if additional biometric data is used as described herein.

Signature Generation and Authentication Process

Figure 7A:
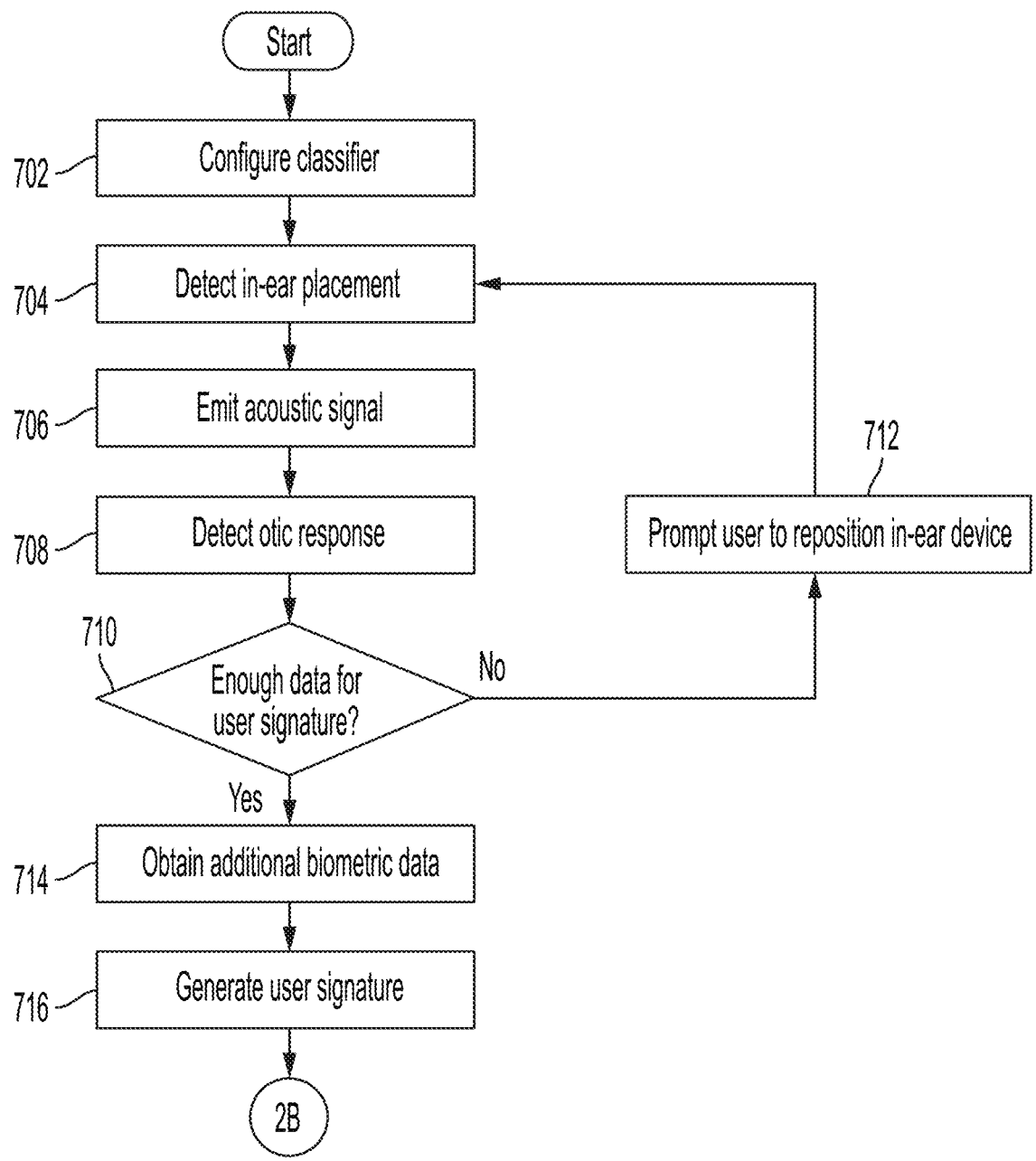
FIGS. 7A-7B are a flow diagram of an example of operations for user authentication via in-ear acoustic measurements according to an embodiment.
Figure 7B:
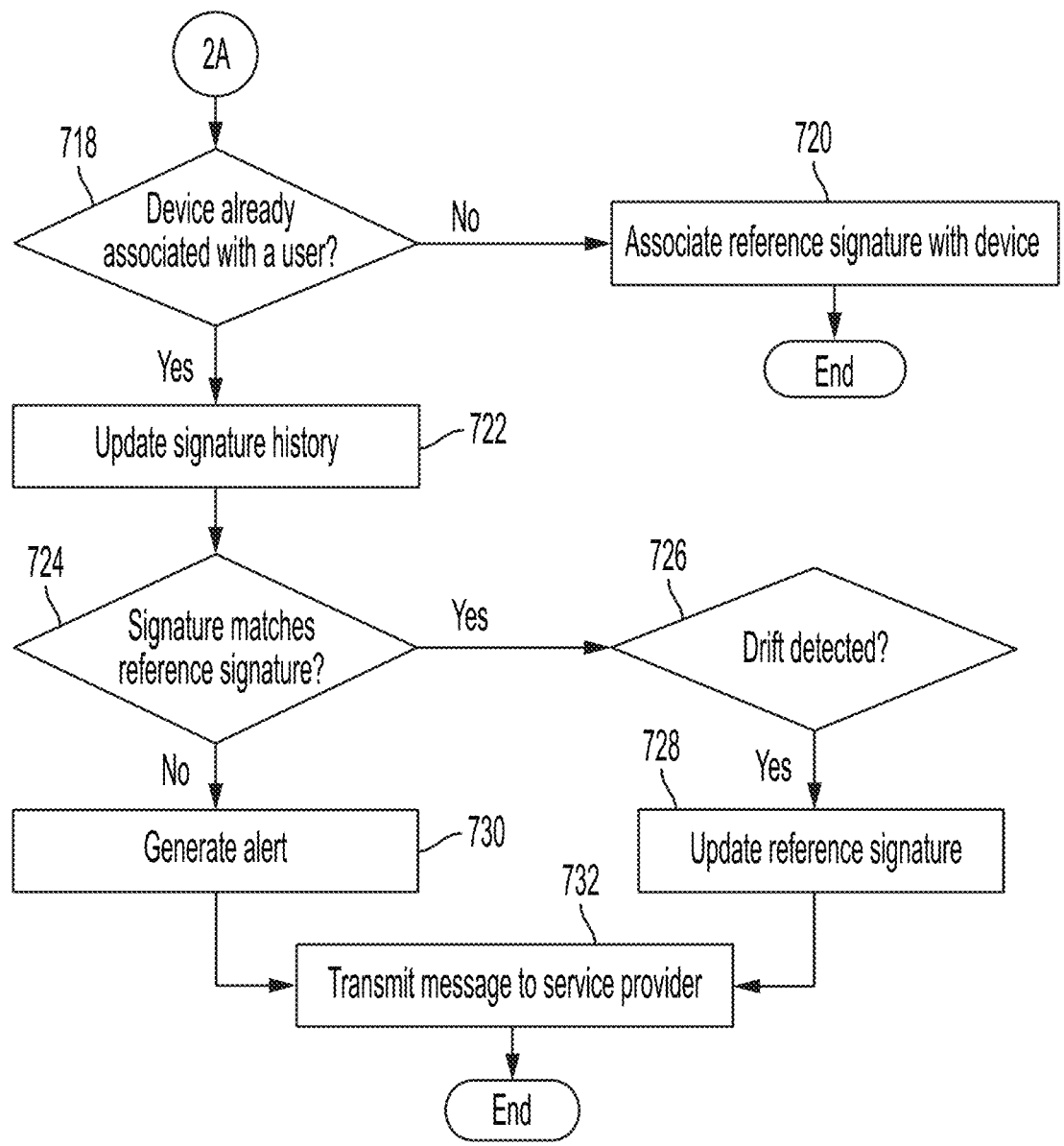

FIG. 7 is a flow diagram of an example of operations for user authentication via in-ear acoustic measurements according to an embodiment. One or more operations illustrated in FIG. 7 may be modified, rearranged, or omitted all together. Accordingly, the particular sequence of operations illustrated in FIG. 7 should not be construed as limiting the scope of one or more embodiments. In the following discussion, operations are described as being performed by a system. Specifically, one or more components of the system 100 illustrated in FIG. 1 may perform these operations.

As described above, user authentication may employ a classification algorithm, which may be based on a static function and/or a machine learning model. If the classifier employs a machine learning model, the system may configure the classifier (Operation 702). Specifically, the system may use machine learning training techniques, described in further detail below, to configure the classifier. The training may be based on a set of training data, e.g., a set of known acoustic measurements that train the machine learning model to classify comparisons of user signatures.

User authentication may be an automated process that initiates when the in-ear device is placed or "fitted" into a user's ear. The in-ear device may include one or more sensors configured to detect placement of the in-ear device in the user's ear. For example, the in-ear device may include a proximity sensor that is triggered when the in-ear device is inserted in the user's ear. The in-ear device may thus detect when it is placed in-ear (Operation 704). Alternatively, user authentication may occur when the in-ear device is powered on and/or in response to user input.

To compute a user signature, the in-ear device emits an acoustic signal into the ear (Operation 706). Based on different anatomies (e.g., differently-shaped ear canals), the otic responses will differ from one ear to the next. The in-ear device detects the otic response (Operation 708). In some cases, user signatures are based on multiple otic responses. For example, an average of measurements taken from multiple fits may be used. The system may determine whether enough data is available to compute a user signature (Operation 710). Enough data may not be available if the user has not yet performed enough fits and/or if a fit does not produce good data (e.g., if the fit is loose or misaligned and produces an otic response that falls outside of acceptable tolerances). The amount of data needed to generate a reference signature may be greater than the amount of data needed to generate a comparison signature that will be compared with the reference signature. For example, six fits may be used to generate a reference signature and a single fit may be used to generate a comparison signature.

If enough data is not yet available, the user may be prompted to reposition the in-ear device (Operation 712). Repositioning the in-ear device may involve removing the device and reinserting it. Alternatively or additionally, multiple otic responses may be obtained without removing the device from the ear. In some examples, each fit corresponds to an independent instance of inserting the device into the ear. Removing and reinserting the in-ear device for each measurement may help account for small variations in how the device is fitted between uses. The process of emitting an acoustic signal and detecting the otic response may be repeated until sufficient data is available.

In an embodiment, the system is configured to obtain additional biometric data (Operation 714). The system may obtain additional biometric data before, after, and/or during the process of obtaining acoustic measurements. The additional biometric data may include one or more of a still image, video, a fingerprint reading, a temperature, an odor, and/or another kind of biometric data or combination thereof. As one example, the additional biometric data may include prompting the user to speak and capturing the sound using the in-ear device's microphone, thus obtaining a metric of acoustic disturbance through the user's head. As another example, the additional biometric data may include measuring distortion product otoacoustic emissions (DPOE's). One or more biometric measurements may use a different microphone than that used to detect otic responses; for example, a separate microphone may be situated on the external surface of the in-ear device, or in another device such as a smartphone, tablet, or personal computer. As another example, an infrared sensor may be used to detect the physical shape inside the user's ear. As another example, an accelerometer may be used to determine a movement "signature" corresponding to the user's typical movement patterns. As another example, a pressure sensor may be used to determine a touch "signature" associated with how the user physically handles the in-ear device. The additional biometric data may be combined with otic response data to generate a user signature and/or may be used as an independent verification of the user's identity (i.e., to help reduce the incidence of false positives and/or false negatives). Alternatively or additionally, global positioning system (GPS) data may be used to confirm that the in-ear device is at a location associated with the intended user (e.g., the user's home or workplace).

The system generates a user signature (Operation 716), based on the acoustic measurements and optionally additional biometric data. Generating a user signature may be based on one or more transfer functions as described above. Alternatively or additionally, a different kind of algorithm may be used. A user signature may be based on a combination of data from both ears. Alternatively, separate signatures may be generated for each ear. Alternatively, a user signature may be based on data only for a single ear.

As discussed above, the system may store a reference signature that is used to authenticate comparison signatures (i.e., signatures computed based on later instances of a user placing the in-ear device in their ear). Generating a reference signature may be performed during initialization/setup of the in-ear device. The system may determine whether the in-ear device is already associated with a user (Operation 718), i.e., whether a reference signature is already stored for the in-ear device. If the in-ear device is not already associated with a user, then the system may associate the in-ear device with a user by storing the user signature as a reference signature (Operation 720).

In some cases, generating a reference signature may be performed under supervision of a professional who is not a user of the in-ear device. For example, if the in-ear device is a hearing aid, generating the reference signature may be performed in a doctor's office, during an initial fitting/configuration of the hearing aid. Generating the reference signature under professional supervision ensures that the reference signature is for the intended individual, thus helping to reduce the incidence of insurance fraud.

In general, embodiments discussed herein assume that an in-ear device is intended for a single user. However, in some embodiments, an in-ear device may have multiple users. For example, a commercial earbud may be configured to support multiple users. In such cases, the system may generate multiple reference signatures, i.e., one for each intended user.

As noted above, the system may be configured to maintain a signature history. Upon obtaining otic response data, the system updates the signature history (Operation 722). The system may update the signature history whether the data is for a reference signature or a comparison signature. The signature history may store user signatures and/or underlying data used to compute user signatures.

If the user signature computed as described above is a comparison signature, the system determines whether the comparison signature matches the reference signature (Operation 724). As used herein, "matching" may not require a precise mathematical match, but a sufficiently close match to indicate a substantial likelihood that the comparison signature and reference signature are from the same ear. For example, a distance metric as described above may be compared with a threshold distance. If the distance exceeds the threshold distance, then the signatures do not match. In the case of a multi-user in-ear device, the system may compare the comparison signature with multiple reference signatures, to determine which (if any) of the intended users is currently using the in-ear device.

If the comparison signature matches the reference signature to a reasonable degree of certainty, then the signatures are presumed to be from the same ear. The match may simply indicate that the in-ear device is being used as intended (e.g., if the in-ear device is a hearing aid intended for use by a particular patient). Alternatively, for a multi-user device, the match may indicate which of multiple user-specific presets to use (e.g., channel presets, virtual assistant settings, volume and/or equalization settings, etc.). Alternatively or additionally, the match may be used to authenticate access to another system, such as to unlock a device, login to a website, etc.

Even if a comparison signature matches a reference signature, user signatures from the same ear may "drift" over time. For example, as ear geometry changes over time (perhaps due to the aging process and/or cerumen accumulation), the corresponding transfer functions may drift accordingly (e.g., based on average or median values over a certain number of most recent measurements). A slow rate of change may indicate drift while a rapid rate of change may indicate that the in-ear device has changed users. The system may be configured to detect drift (Operation 726) and, if drift is detected, update the reference signature to account for the drift (Operation 728). If the reference signature is not updated to account for drift, the incidence of false negatives may increase over time. Thus, updating the reference signature to account for drift may help preserve the system's accuracy for a particular user.

If the comparison signature does not match the reference signature to a reasonable degree of certainty, then the signatures are presumed to be from different ears, indicating that the in-ear device has changed users. In the case of an in-ear device used by multiple users, this mismatch may indicate that no presets are available for the current user. In the case of authenticating a user to access a device (e.g., a smartphone or other device), website, etc., the mismatch may indicate that the current user is not authorized to access that device, website, etc. In the case of a hearing aid, the mismatch may indicate that the hearing aid is not being used by the intended user.

In some cases, use of the in-ear device is managed and/or monitored by a service provider, such as a medical professional and/or medical insurance company. When a mismatch between user signatures occur, the system may generate an alert directed to the service provider (Operation 730). The system may transmit a message to the service provider (Operation 732) that includes the alert. The alert may prompt the service provider, for example, to review the account associated with the in-ear device. The service provider may reach out (e.g., by phone or email) to the intended user, to try to determine the root cause (e.g., a defective device, insurance fraud, or some other cause) of the mismatch. Even when user signatures match, the system may transmit messages to the service provider, to provide the service provider with useful information about when and how the in-ear device is being used. The amount and kinds of data transmitted to the service provider may depend, at least in part, on a user's prior consent to a data sharing policy. For example, such messaging may be a condition of a discounted price for a hearing aid. Being able to authenticate users of hearing aids, as described herein, may increase the likelihood that insurance companies provide coverage for hearing aids, thus improving access to such devices for those in need. In addition, the ability to confirm that a patient is actually using their hearing aid may increase compliance. An insurance company may offer discounted rates for those with higher compliance.

Machine Learning

In embodiment, a machine learning engine trains a machine learning model to perform one or more operations, e.g., comparing user signatures. Training a machine learning model uses training data to generate a function that, given one or more inputs to the machine learning model, computes a corresponding output. The output may correspond to a prediction based on prior machine learning. In an embodiment, the output includes a label, classification, and/or categorization assigned to the provided input(s). The machine learning model corresponds to a learned model for performing the desired operation(s) (e.g., labeling, classifying, and/or categorizing inputs). A system may use multiple machine learning engines and/or multiple machine learning models for different purposes. A machine learning engine may be part of an in-ear device, over-the-ear device, general-purpose device, server, and/or another kind of device or combination thereof.

In an embodiment, the machine learning engine may use supervised learning, semi-supervised learning, unsupervised learning, reinforcement learning, and/or another training method or combination thereof. In supervised learning, labeled training data includes input/output pairs in which each input is labeled with a desired output (e.g., a label, classification, and/or categorization), also referred to as a supervisory signal. For example, labeled data may include otic response data associated with known users, to help train a classifier to determine whether user signatures come from the same ear. In semi-supervised learning, some inputs are associated with supervisory signals and other inputs are not associated with supervisory signals. In unsupervised learning, the training data does not include supervisory signals. Reinforcement learning uses a feedback system in which the machine learning engine receives positive and/or negative reinforcement in the process of attempting to solve a particular problem (e.g., to optimize performance in a particular scenario, according to one or more predefined performance criteria). In an embodiment, the machine learning engine initially uses supervised learning to train the machine learning model and then uses unsupervised learning to update the machine learning model on an ongoing basis.

In an embodiment, a machine learning engine may use many different techniques to label, classify, and/or categorize inputs. A machine learning engine may transform inputs into feature vectors that describe one or more properties ("features") of the inputs. The machine learning engine may label, classify, and/or categorize the inputs based on the feature vectors. Alternatively or additionally, a machine learning engine may use clustering (also referred to as cluster analysis) to identify commonalities in the inputs. The machine learning engine may group (i.e., cluster) the inputs based on those commonalities. The machine learning engine may use hierarchical clustering, k-means clustering, and/or another clustering method or combination thereof. In an embodiment, a machine learning engine includes an artificial neural network. An artificial neural network includes multiple nodes (also referred to as artificial neurons) and edges between nodes. Edges may be associated with corresponding weights that represent the strengths of connections between nodes, which the machine learning engine adjusts as machine learning proceeds. Alternatively or additionally, a machine learning engine may include a support vector machine. A support vector machine represents inputs as vectors. The machine learning engine may label, classify, and/or categorizes inputs based on the vectors. Alternatively or additionally, the machine learning engine may use a naïve Bayes classifier to label, classify, and/or categorize inputs. Alternatively or additionally, given a particular input, a machine learning model may apply a decision tree to predict an output for the given input. Alternatively or additionally, a machine learning engine may apply fuzzy logic in situations where labeling, classifying, and/or categorizing an input among a fixed set of mutually exclusive options is impossible or impractical. The aforementioned machine learning model and techniques are discussed for exemplary purposes only and should not be construed as limiting one or more embodiments.

Computer Systems, Networks, and Cloud Computing

In an embodiment, a system includes one or more devices, including one or more hardware processors, that are configured to perform any of the operations described herein and/or recited in any of the claims.

In an embodiment, one or more non-transitory computer-readable storage media store instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 8:
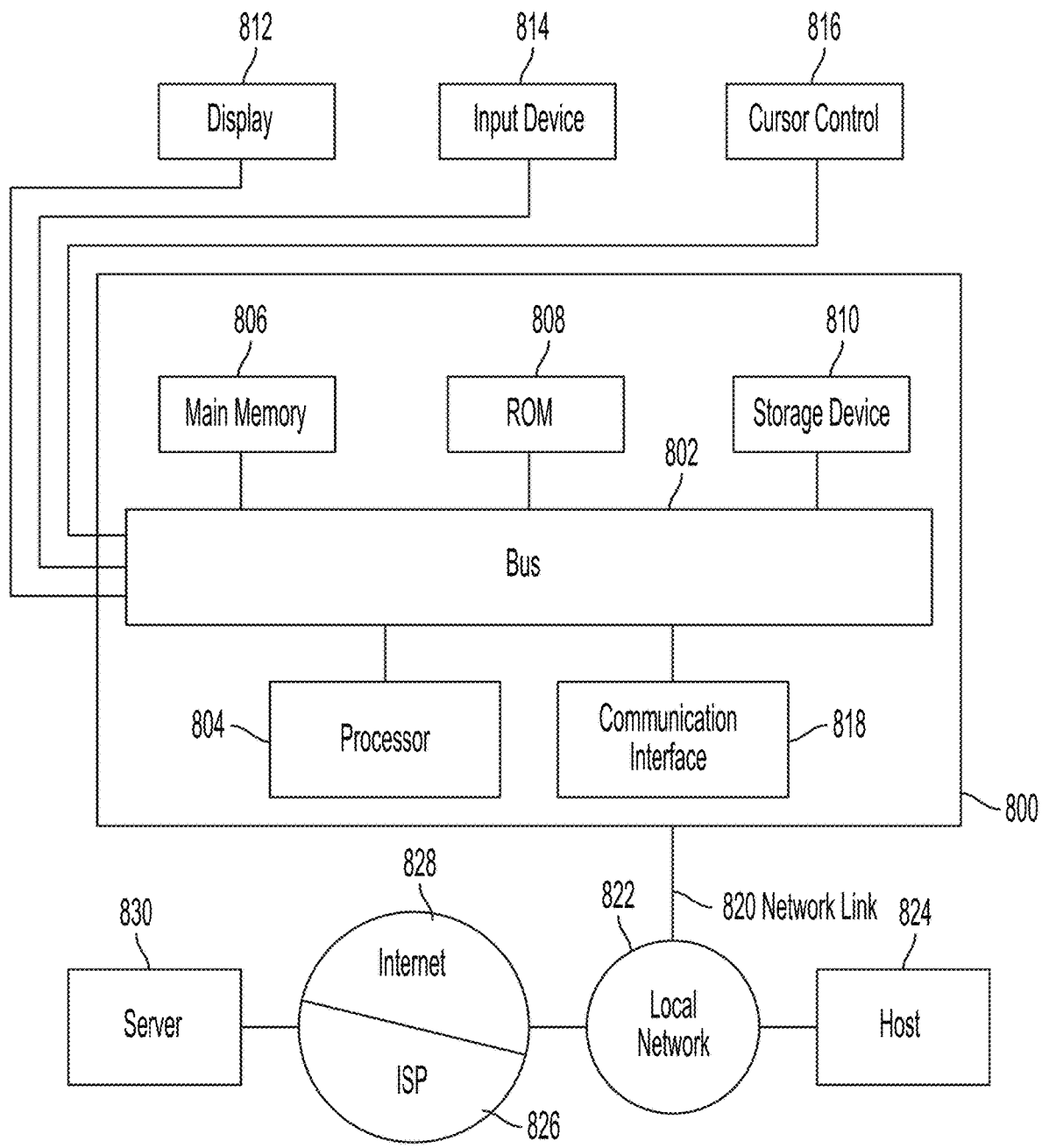
FIG. 8 is a block diagram of an example of a computer system according to an embodiment.

For example, FIG. 8 is a block diagram of an example of a computer system 800 according to an embodiment. Computer system 800 includes a bus 802 or other communication mechanism for communicating information, and one or more hardware processor(s) 804 coupled with the bus 802 for processing information. Hardware processor(s) 804 may include a general-purpose microprocessor.

Computer system 800 also includes a main memory 806, such as a random access memory (RAM) or other dynamic storage device, coupled to bus 802 for storing information and instructions to be executed by processor(s) 804. Main memory 806 also may be used for storing temporary variables or other intermediate information during execution of instructions to be executed by processor(s) 804. Such instructions, when stored in one or more non-transitory storage media accessible to processor(s) 804, render computer system 800 into a special-purpose machine that is customized to perform the operations specified in the instructions.

Computer system 800 further includes a read only memory (ROM) 808 or other static storage device coupled to bus 802 for storing static information and instructions for processor(s) 804. A storage device 810, such as a magnetic disk or optical disk, is provided and coupled to bus 802 for storing information and instructions.

Computer system 800 may be coupled via bus 802 to a display 812, such as a liquid crystal display (LCD), plasma display, electronic ink display, cathode ray tube (CRT) monitor, or any other kind of device for displaying information to a computer user. An input device 814, including alphanumeric and other keys, may be coupled to bus 802 for communicating information and command selections to processor(s) 804. Alternatively or additionally, computer system 800 may receive user input via a cursor control 816, such as a mouse, a trackball, a trackpad, or cursor direction keys for communicating direction information and command selections to processor(s) 804 and for controlling cursor movement on display 812. This input device typically has two degrees of freedom in two axes, a first axis (e.g., x) and a second axis (e.g., y), that allows the device to specify positions in a plane. Alternatively or additionally, computer system 9 may include a touchscreen. Display 812 may be configured to receive user input via one or more pressure-sensitive sensors, multi-touch sensors, and/or gesture sensors. Alternatively or additionally, computer system 800 may receive user input via a microphone, video camera, and/or some other kind of user input device (not shown).

Computer system 800 may implement the techniques described herein using customized hard-wired logic, one or more ASICs or FPGAs, firmware, and/or program logic which in combination with other components of computer system 800 causes or programs computer system 800 to be a special-purpose machine. According to one embodiment, the techniques herein are performed by computer system 800 in response to processor(s) 804 executing one or more sequences of one or more instructions contained in main memory 806. Such instructions may be read into main memory 806 from another storage medium, such as storage device 810. Execution of the sequences of instructions contained in main memory 806 causes processor(s) 804 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 810. Volatile media includes dynamic memory, such as main memory 806. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 802. Transmission media may also take the form of acoustic or light waves, such as those generated during radio-wave and infra-red data communications.

Various forms of media may be involved in carrying one or more sequences of one or more instructions to processor(s) 804 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 800 may receive the data from the network and place the data on bus 802. Bus 802 carries the data to main memory 806, from which processor(s) 804 retrieves and executes the instructions. The instructions received by main memory 806 may optionally be stored on storage device 810 either before or after execution by processor(s) 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN. Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822, and communication interface 818.

The received code may be executed by processor(s) 804 as it is received, and/or stored in storage device 810, or other non-volatile storage for later execution.

In an embodiment, a computer network provides connectivity among a set of nodes running software that utilizes techniques as described herein. The nodes may be local to and/or remote from each other. The nodes are connected by a set of links. Examples of links include a coaxial cable, an unshielded twisted cable, a copper cable, an optical fiber, and a virtual link.

A subset of nodes implements the computer network. Examples of such nodes include a switch, a router, a firewall, and a network address translator (NAT). Another subset of nodes uses the computer network. Such nodes (also referred to as "hosts") may execute a client process and/or a server process. A client process makes a request for a computing service (for example, a request to execute a particular application and/or retrieve a particular set of data). A server process responds by executing the requested service and/or returning corresponding data.

A computer network may be a physical network, including physical nodes connected by physical links. A physical node is any digital device. A physical node may be a function-specific hardware device. Examples of function-specific hardware devices include a hardware switch, a hardware router, a hardware firewall, and a hardware NAT. Alternatively or additionally, a physical node may be any physical resource that provides compute power to perform a task, such as one that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (for example, a physical network). Each node in an overlay network corresponds to a respective node in the underlying network. Accordingly, each node in an overlay network is associated with both an overlay address (to address the overlay node) and an underlay address (to address the underlay node that implements the overlay node). An overlay node may be a digital device and/or a software process (for example, a virtual machine, an application instance, or a thread). A link that connects overlay nodes may be implemented as a tunnel through the underlying network. The overlay nodes at either end of the tunnel may treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware and/or software configured to execute server processes. Examples of network resources include a processor, a data storage, a virtual machine, a container, and/or a software application. Network resources may be shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). In a hybrid cloud, a computer network includes a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, a system supports multiple tenants. A tenant is a corporation, organization, enterprise, business unit, employee, or other entity that accesses a shared computing resource (for example, a computing resource shared in a public cloud). One tenant (through operation, tenant-specific practices, employees, and/or identification to the external world) may be separate from another tenant. The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In an embodiment, in a multi-tenant computer network, tenant isolation is implemented to ensure that the applications and/or data of different tenants are not shared with each other. Various tenant isolation approaches may be used. In an embodiment, each tenant is associated with a tenant ID. Applications implemented by the computer network are tagged with tenant ID's. Additionally or alternatively, data structures and/or datasets, stored by the computer network, are tagged with tenant ID's. A tenant is permitted access to a particular application, data structure, and/or dataset only if the tenant and the particular application, data structure, and/or dataset are associated with a same tenant ID. As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants. A subscription list may indicate which tenants have authorization to access which applications. For each application, a list of tenant ID's of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels may be used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

What is claimed is:

1. One or more non-transitory computer-readable media storing instructions that, when executed by one or more processors, cause:

emitting, by an in-ear device, a first acoustic signal;

detecting, by the in-ear device, a first otic response to the first acoustic signal;

generating a first user signature, based at least on the first otic response to the first acoustic signal;

performing a comparison of the first user signature and a second user signature associated with the in-ear device, to determine whether the in-ear device has changed users, wherein performing the comparison includes:

determining a difference between the first user signature and the second user signature in a frequency domain at each of a plurality of frequencies of the first user signature and the second user signature, determining a similarity metric between the first user signature and the second user signature based on the difference between the first user signature and the second user signature in the frequency domain at at least one frequency of the plurality of frequencies of the first user signature and the second user signature, and determining whether the in-ear device has changed users by comparing the similarity metric to a classification threshold; and responsive to determining that the in-ear device has changed users, transmitting an alert to an entity that provides one or more services associated with the in-ear device.

2. The one or more non-transitory computer-readable media of claim 1, further storing instructions that, when executed by one or more processors, cause:
  emitting, by the in-ear device, a second acoustic signal;
  detecting, by the in-ear device, a second otic response the second acoustic signal; and
  generating the second user signature as a reference signature for user authentication, based at least on the second otic response to the second acoustic signal.

3. The one or more non-transitory computer-readable media of claim 1, further storing instructions that, when executed by one or more processors, cause:
  determining, based on the comparison of the first user signature and the second user signature, that the in-ear device has changed users.

4. The one or more non-transitory computer-readable media of claim 1, wherein the in-ear device is a medical hearing aid and the entity that provides one or more services associated with the in-ear device is a medical insurance provider.

5. The one or more non-transitory computer-readable media of claim 1, wherein:
  the first acoustic signal is one of a plurality of acoustic signals emitted by the in-ear device during a signature generation session;
  the first otic response is one of a plurality of otic responses, associated respectively with the plurality of acoustic signals, detected during the signature generation session; and
  generating the first user signature comprises computing the first user signature as a function of at least the plurality of otic responses.

6. The one or more non-transitory computer-readable media of claim 5, wherein the in-ear device is configured to generate the plurality of acoustic signals and detect the plurality of otic responses over a plurality of instances of inserting the in-ear device into an ear during the signature generation session.

7. The one or more non-transitory computer-readable media of claim 1, further storing instructions that, when executed by one or more processors, cause:
  detecting a drift in otic responses of an ear of a user, over a plurality of signature generation sessions; and
  responsive to detecting the drift in otic responses of the ear, updating a reference user signature for the user to reflect the drift.

8. The one or more non-transitory computer-readable media of claim 1, wherein determining the similarity metric between the first user signature and the second user signature based on the difference between the first user signature and the second user signature in the frequency domain at the at least one frequency of the plurality of frequencies of the first user signature and the second user signature includes determining the similarity metric based on the difference between the first user signature and the second user signature in the frequency domain at each frequency of the plurality of frequencies of the first user signature and the second user signature.

9. A system comprising:
  at least one device including one or more processors; and
  the system being configured to perform operations comprising:
    emitting, by an in-ear device, a first acoustic signal;
    detecting, by the in-ear device, a first otic response to the first acoustic signal;
    generating a first user signature, based at least on the first otic response to the first acoustic signal;
    performing a comparison of the first user signature and a second user signature associated with the in-ear device, to determine whether the in-ear device has changed users, wherein performing the comparison includes:
      determining a difference between the first user signature and the second user signature in a frequency domain at each of a plurality of frequencies of the first user signature and the second user signature,
      determining a similarity metric between the first user signature and the second user signature based on the difference between the first user signature and the second user signature in the frequency domain at at least one frequency of the plurality of frequencies of the first user signature and the second user signature, and
      determining whether the in-ear device has changed users by comparing the similarity metric to a classification threshold; and
    responsive to determining that the in-ear device has changed users, transmitting an alert to an entity that provides one or more services associated with the in-ear device.

10. The system of claim 9, the operations further comprising:
  emitting, by the in-ear device, a second acoustic signal;
  detecting, by the in-ear device, a second otic response the second acoustic signal; and
  generating the second user signature as a reference signature for user authentication, based at least on the second otic response to the second acoustic signal.

11. The system of claim 9, the operations further comprising:
  determining, based on the comparison of the first user signature and the second user signature, that the in-ear device has changed users.

12. The system of claim 9, wherein the in-ear device is a medical hearing aid and the entity that provides one or more services associated with the in-ear device is a medical insurance provider.

13. The system of claim 9, wherein:
  the first acoustic signal is one of a plurality of acoustic signals emitted by the in-ear device during a signature generation session;
  the first otic response is one of a plurality of otic responses, associated respectively with the plurality of acoustic signals, detected during the signature generation session; and
  generating the first user signature comprises computing the first user signature as a function of at least the plurality of otic responses.

14. The system of claim 13, wherein the in-ear device is configured to generate the plurality of acoustic signals and detect the plurality of otic responses over a plurality of instances of inserting the in-ear device into an ear during the signature generation session.

15. The system of claim 9, the operations further comprising:
  detecting a drift in otic responses of an ear of a user, over a plurality of signature generation sessions; and
  responsive to detecting the drift in otic responses of the ear, updating a reference user signature for the user to reflect the drift.

16. A method comprising:
  emitting, by an in-ear device, a first acoustic signal;
  detecting, by the in-ear device, a first otic response to the first acoustic signal;

generating a first user signature, based at least on the first otic response to the first acoustic signal;

performing a comparison of the first user signature and a second user signature associated with the in-ear device, to determine whether the in-ear device has changed users, wherein performing the comparison includes:

determining a difference between the first user signature and the second user signature in a frequency domain at each of a plurality of frequencies of the first user signature and the second user signature, determining a similarity metric between the first user signature and the second user signature based on the difference between the first user signature and the second user signature in the frequency domain at at least one frequency of the plurality of frequencies of the first user signature and the second user signature, and determining whether the in-ear device has changed users by comparing the similarity metric to a classification threshold; and responsive to determining that the in-ear device has changed users, transmitting an alert to an entity that provides one or more services associated with the in-ear device.

17. The method of claim 16, further comprising:

emitting, by the in-ear device, a second acoustic signal;

detecting, by the in-ear device, a second otic response the second acoustic signal; and generating the second user signature as a reference signature for user authentication, based at least on the second otic response to the second acoustic signal.

18. The method of claim 16, further comprising:

determining, based on the comparison of the first user signature and the second user signature, that the in-ear device has changed users.

19. The method of claim 16, wherein:

the first acoustic signal is one of a plurality of acoustic signals emitted by the in-ear device during a signature generation session;

the first otic response is one of a plurality of otic responses, associated respectively with the plurality of acoustic signals, detected during the signature generation session; and generating the first user signature comprises computing the first user signature as a function of at least the plurality of otic responses.

20. The method of claim 19, wherein the in-ear device is configured to generate the plurality of acoustic signals and detect the plurality of otic responses over a plurality of instances of inserting the in-ear device into an ear during the signature generation session.

21. The method of claim 16, the operations further comprising:

detecting a drift in otic responses of an ear of a user, over a plurality of signature generation sessions; and responsive to detecting the drift in otic responses of the ear, updating a reference user signature for the user to reflect the drift.

* * * * *